(12) United States Patent
Hiban et al.

(10) Patent No.: US 11,857,508 B2
(45) Date of Patent: Jan. 2, 2024

(54) ISOTROPIC CONCENTRATE AND WASH COMPOSITIONS

(71) Applicant: Conopco, Inc., Englewood Cliffs, NJ (US)

(72) Inventors: Douglas John Hiban, Newtown, CT (US); Tirucherai Varahan Vasudevan, Bethany, CT (US); Mingchang Ye, Stratford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 17/793,989

(22) PCT Filed: Jan. 20, 2021

(86) PCT No.: PCT/EP2021/051124
§ 371 (c)(1),
(2) Date: Jul. 20, 2022

(87) PCT Pub. No.: WO2021/148428
PCT Pub. Date: Jul. 29, 2021

(65) Prior Publication Data
US 2023/0045405 A1     Feb. 9, 2023

Related U.S. Application Data

(60) Provisional application No. 62/963,937, filed on Jan. 21, 2020.

(51) Int. Cl.
| | | |
|---|---|---|
| *A61K 8/00* | (2006.01) | |
| *A61K 8/46* | (2006.01) | |
| *A61K 8/34* | (2006.01) | |
| *A61Q 19/10* | (2006.01) | |

(52) U.S. Cl.
CPC .............. *A61K 8/466* (2013.01); *A61K 8/345* (2013.01); *A61Q 19/10* (2013.01)

(58) Field of Classification Search
CPC .................................. A61K 8/466; A61K 8/345
See application file for complete search history.

(56) References Cited

U.S. PATENT DOCUMENTS

| | | |
|---|---|---|
| 5,393,466 A | 2/1995 | Ilardi et al. |
| 5,415,810 A | 5/1995 | Lee |
| 5,925,603 A | 7/1999 | D Angelo |
| 6,117,628 A | 9/2000 | Eichorst et al. |
| 8,440,605 B2 | 5/2013 | Wise |
| 8,794,474 B2 | 8/2014 | Mueller et al. |
| 2008/0153730 A1 | 6/2008 | Tsaur |
| 2016/0000669 A1 | 1/2016 | Hinman et al. |
| 2016/0167293 A1 | 6/2016 | Bush et al. |
| 2010/6296442 | 10/2016 | L'Oreal |
| 2016/0310388 A1 | 10/2016 | Smith, III et al. |
| 2017/0304173 A1 | 10/2017 | Elder |
| 2018/0098923 A1 | 4/2018 | Hutton, III |
| 2018/0280270 A1* | 10/2018 | Rughani ................ A61K 8/416 |
| 2019/0031258 A1 | 1/2019 | Soik et al. |
| 2019/0077578 A1* | 3/2019 | Eungrasamee ........ B65D 25/16 |
| 2019/0282480 A1* | 9/2019 | Su ........................... C11D 1/88 |

FOREIGN PATENT DOCUMENTS

| | | |
|---|---|---|
| CN | 102459554 | 5/2012 |
| EP | 0133345 | 2/1985 |
| EP | 2532343 | 12/2012 |
| EP | 2552391 | 3/2018 |
| FR | 3012962 | 11/2013 |
| WO | WO9220776 | 11/1992 |
| WO | WO2011117650 | 9/2011 |
| WO | WO2011120780 | 10/2011 |
| WO | WO2013150300 | 10/2013 |
| WO | WO2019011521 | 1/2019 |
| WO | WO2020025275 | 2/2020 |

OTHER PUBLICATIONS

Nanofibrillated cellulose surface modification and potential applications; 2014; 5-31; 292.
Sun et al.; Journal of Cosmetic Science; 2003; 559-568; 54.
Search Report & Written Opinion in EP20168571; dated Sep. 24, 2020.
Search Report and Written Opinion in PCTEP2021051124; dated Apr. 29, 2021.
Search Report and Written Opinion in PCTEP2021051123; dated Mar. 1, 2021.
Written Opinion of the IPEA in PCT/EP/2021/051124; dated Dec. 20, 2021.
Can coconut oil prevent hair fall; Nov. 25, 2018; 1-6.

* cited by examiner

Primary Examiner — Necholus Ogden, Jr.
(74) Attorney, Agent, or Firm — Edward A. Squillante

(57) ABSTRACT

The present invention relates to an isotropic concentrate composition that is easy to hydrate and transform into an end use wash composition. The end use wash composition resulting from the concentrate composition is suitable for topical application and for hand washing. The concentrate comprises fragrance oil and emulsifier at levels that unexpectedly result in a concentrate composition and end use composition that are free of ingredient precipitation that interferes with the appearance and usage of the compositions.

13 Claims, No Drawings

ISOTROPIC CONCENTRATE AND WASH COMPOSITIONS

FIELD OF THE INVENTION

The present invention relates to an isotropic concentrate composition that is easy to hydrate and transform into an end use wash composition. The end use wash composition resulting tom the concentrate composition is suitable for topical application and for washing, especially the hands. In particular, the invention relates to a composition which, at least in one embodiment, is preferably sulfate free, and mild when used. Moreover, the end use composition made from the concentrate is surprisingly able to lather appreciably, is stable and also has a micellar (isotropic) microstructure. The concentrate comprises fragrance oil and emulsifier at levels that unexpectedly result in a concentrate composition and end use composition that are free of any ingredient precipitation that interferes with the appearance and usage of the compositions. Such an end use composition also provides excellent sensory benefits.

BACKGROUND OF THE INVENTION

Consumers seek personal cleansing compositions that are preferably sulfate free (i.e., having no sulfate-based surfactants) and that are mild and moisturizing while delivering superior sensory benefits such as enjoyable lather and soft, smooth skin, even after one washing. This is especially true when it comes to washing the hands since consumers are encouraged to frequently wash their hands to avoid getting sick.

In addition to the above, conscious consumers are looking for opportunities to reduce environmental waste, and particularly, waste associated with plastics, given it is often publicized that the world's oceans will soon have more plastic than fish. In view of environmental concerns and the desire for consumers and conscious companies to do more for the planet, there is a strong desire to use less plastic when selling products, including consumer products. Efforts, therefore, have been made to sell product in concentrate form, and to ship product that comprises less water in it. The difficulty with concentrates is consumers often do not like adding additional water to the concentrate and further work, like stirring, to convert the concentrate into an end usable product. As to the hydrated product, common complaints include that the product is time consuming to prepare, not homogeneous and grainy with precipitate after adding water and during use.

It is of increasing interest to develop a concentrate that is easy to use with refillable packaging and easy to hydrate. It is also desirable to provide to consumers a product that is ready to use in under five (5) minutes and provides desirable sensory characteristics without being grainy. The concentrate and end use composition of the present invention comprise acyl isethionates. These surfactants are known to be mild surfactants. However, compositions containing high levels of acyl isethionates and other surfactants often display ingredient precipitation (e.g., crystallization) which typically leads to an end use composition that is not desirable for consumer use. This invention, therefore, is directed to an isotropic concentrate composition suitable for dilution into an end use wash composition which is also isotropic. The concentrate composition comprises fragrance oil and emulsifier at levels such that upon dilution unexpectedly results in an end use composition that is free of ingredient precipitation, even when formulated with acyl isethionate.

Additional Information

Efforts have been disclosed for making wash compositions. In Sun et al (Journal of Cosmetic Science, 54, 559-568, 2003), wash compositions with acyl isethionates and other surfactants like methyl acyl taurates, acyl glutamates, acyl lactylates, alkyl ether and dialkyl sulfosuccinates, and acyl sarcosinates are described.

Even other efforts have been disclosed for making wash compositions. In U.S. Pat. No. 5,415,810 to Lee et al., disclosed are acyl isethionate containing wash liquids that also contain other anionic surfactants such as methyl acyl taurates.

Still other efforts have been disclosed for making wash compositions. In U.S. Pat. No. 5,925,603 to D'Angelo, disclosed is the use of methyl acyl taurate with acyl isethionates.

Further efforts have been described for making wash compositions. In WO1992020776A1 and EP0133345A1, liquid hand soap compositions are described. In U.S. Pat. No. 6,117,828, hand wash compositions with wheat protein are described.

None of the Additional Information describes a concentrate composition or end use composition as claimed herein.

SUMMARY OF THE INVENTION

In a first aspect, the present invention is directed to an isotropic concentrate composition comprising:
1) 0.1 to 10%, preferably, 0.5 to 6%, more preferably, 1 to 4.5% by weight. of acyl isethionate;
2) 0.1% to 10%, preferably, 0.5 to 6%, more preferably, 1 to 4.5% by weight acyl taurate;
3) 0.2 to 25%, preferably, 3.0 to 20% and more preferably, 5 to 17% by weight of an amphoteric and/or zwitterionic surfactant;
4) 5.0 to 50%, preferably, 10.0 to 40%, more preferably, 20 to 30% by weight humectant comprising glycerin;
5) 0.7 to 8%, preferably, 1.0 to 7%, more preferably, 1.5 to 5% by weight fragrance;
6) 0.7 to 5%, preferably, 1.0 to 4.5%, more preferably, 1.2 to 4% by weight emulsifier having an HLB from 8 to 19, preferably, from 10 to 18, more preferably, from 12 to 17; and
7) 25 to 80%, preferably, 30 to 70%, more preferably, 35 to 45% by weight water, wherein total surfactant makes up from 12 to 35%, and preferably, from 15 to 30%, and most preferably, from 20 to 28% by weight of the isotropic concentrate composition and further wherein emulsifier and fragrance are at an emulsifier to fragrance weight ratio from 1:0.8 to 1:4, preferably, from 1:1 to 1:3, and more preferably, from 1:1.1 to 1:2.

In a second aspect, the present invention is directed to an end use composition prepared by hydrating the isotropic concentrate composition of the first aspect of the invention, where isotropic concentrate composition to water added is at a weight ratio from 1:1 to 1:6, preferably, 1:1.5 to 1:5, more preferably, 1:2 to 1:4.

In a third aspect, the present invention is directed to the use of the end use composition as a hand washing composition, preferably a hand washing composition that is dispensed from a refillable package, and more preferably, from a refillable package suitable to discharge hand washing composition in the form of a foam.

As used herein, "compositions" with no qualifier is meant to mean the isotropic concentrate composition and end use composition of this invention. Hydratable, as used herein, means add and/or add and absorb water even to a composition that has water such as a composition that is initially 25 to 80% by weight water (i.e., to dilute). Free of ingredient precipitation means no visible signs of precipitate or crystal formation in the end use composition of the invention (and no sensation of graininess when applying compositions to skin) for at least 1 to 3 days after mixing, preferably 2-3 days after mixing and forming end use composition. Skin, as used herein, is meant to include skin on the arms (including underarms), face, feet, neck, chest, hands, legs, buttocks and scalp (including hair). Isotropic concentrate composition ("isotropic concentrate") means an isotropic composition that does not increase in viscosity when water is added to the same to thereby yield an end use composition of lower viscosity which is also isotropic and suitable for topical application. The isotropic concentrate is a composition which prior to hydrating often has a viscosity from 30 to 6,500 cps. The end use composition is one suitable to be wiped or washed off, and preferably, washed off with water. The end use composition can be a home care cleaning composition but is preferably a shampoo, make-up wash, facial wash, hand wash or personal care liquid body wash. The end use composition may, optionally, comprise medicinal or therapeutic agents, but preferably, is a wash which is cosmetic and non-therapeutic. In one embodiment of the invention, the end use composition is a home care composition like a table top or toilet cleaning composition. In another embodiment, the end use composition is a shampoo composition. In still another embodiment, the end use composition is preferably a personal wash composition, and especially, a liquid hand wash that is self-foaming and dispensed from a refillable package. As hereinafter described, the end use composition of the present invention may optionally comprise skin benefit ingredients added thereto such as emollients, vitamins and/or derivatives thereof, resorcinols, retinoic acid precursors, colorants, moisturizers, sunscreens, mixtures thereof or the like. The skin benefit ingredients (or agents) may be water or oil soluble. If used, oil soluble skin benefit agents typically make up to 1.5% by weight of the end use composition whereby water soluble skin benefit agents, when used, typically make up to 10% by weight of the end use composition of the present invention. The isotropic concentrate and end use composition typically have a pH from 4.5 to 10. Viscosity, unless noted otherwise, is taken with a Discovery HR-2 Rheometer using sand blasted plates with a 100 micron gap and a shear rate of 4-15 $s^{-1}$. Viscosity is measured at 25° C. Reduction in viscosity means the isotropic concentrate of the present invention will have a starting viscosity that is higher than the final viscosity after water is added and the resulting end use composition is made. The end use composition is made by combining water and isotropic concentrate and mixing (with moderate shear like stirring, preferably shaking) the same to produce the end use composition having a lower viscosity than the isotropic concentrate it is made from. Typically, the end use composition such as a hand wash composition will have a viscosity from 0.0 to 650 cps. In another embodiment, the isotropic concentrate may be applied directly to, for example, a consumer and when water and shear are applied (like, for example, shearing with the hand and water from a sink or shower) the desired end use composition (i.e., hand or body wash) may be made. As used herein, "substantially free of sulfate" means less than 6.0% by weight of the end use composition, and "substantially free of oil" means less than 0.3% by weight of the end use composition where oil does not mean or include any fragrance oil. The term comprising is meant to encompass the terms consisting essentially of and consisting of. For the avoidance of doubt, and for illustration, the end use composition of this invention comprising surfactant, water and active is meant to include a composition consisting essentially of the same and a composition consisting of the same. All ranges defined are meant to include all ranges subsumed therein. Except in the operating comparative examples, or where otherwise explicitly indicated, all numbers in this description indicating amounts or ratios of materials or conditions and/or physical properties of materials and/or use are to be understood as modified by the word "about".

DETAILED DESCRIPTION OF THE PREFERRED EMBODIMENTS

The isotropic concentrate composition of the present invention will have a viscosity from 30 to 6,500 cps, and preferably, from 50 to 3,000 cps, and most preferably, from 100 to 1,500 cps, including all ranges subsumed therein. As to the end use composition, the same has a viscosity from 0.0 to 650 cps, and preferably, from 0 to 500 cps, and most preferably, from 0 to 250 cps, including all ranges subsumed therein. The viscosity of the end use composition ensures that composition may be discharged from a pump dispenser, especially one that dispenses foam, without clogging concerns. Surprisingly, at such viscosities, the end use composition is easily discharged from a dispenser while surprisingly delivering excellent sensory benefits to the consumer.

As to the anionic surfactant, the same in total typically makes up from 0.15 to 30% by weight of the isotropic concentrate, including all ranges subsumed therein. In an embodiment of the invention, the anionic surfactant in total makes up from 0.5 to 16% by weight, and preferably, from to 0.8 to 9% by weight of the isotropic concentrate, including all ranges subsumed therein. Still in another embodiment of the invention, the acyl isethionates and acyl taurates used make up from 75 to 100%, and preferably, from 80 to 100%, and most preferably, from 85 to 100% by weight of the total of anionic surfactant used in the compositions of the present invention. In an optional embodiment of the invention, the total amount of anionic surfactant in the compositions of this invention can comprise from from 0.01 to 7% by weight acyl glycinate in addition to acyl isethionate and acyl taurate, both of which may comprise $C_{1-4}$ alkyl substituents on their head groups, and especially, methyl groups.

As to the amphoteric and/or zwitterionic surfactant used in the isotropic concentrate, the same typically makes up from 0.2 to 25%, and preferably, from 3 to 20%, and most preferably, from 5 to 17% by weight of the isotropic concentrate, including all ranges subsumed therein.

To, for example, aid in isotropic concentrate structuring and hydration, structuring agent like $C_6$-$C_{18}$ acid and/or alcohol (i.e., derivative thereof) can preferably be used and typically make up from 0.1 to 3%, and preferably, from 0.2 to 2%, and most preferably, from 0.4 to 1.5% by weight of the isotropic concentrate, including all ranges subsumed therein. The preferred structuring agent is myristic acid, lauric acid, stearic acid, or any alcohol derivative thereof or mixture thereof. In an embodiment of the invention, the structuring agent comprises lauric acid and stearic acid at a lauric acid to stearic acid weight ratio from 1:1 to 1:5, preferably from 1:1 to 1:4, and most preferably, from 1:1 to 1:3, including all ratios subsumed therein.

Inorganic salt is an optional ingredient suitable for use to aid in composition sensory characteristic delivery. Typical salts that may be used include NaCl, KCl, $MgCl_2$, $CaCl_2$, mixtures thereof or the like. Typically, the inorganic salt makes up from 0 to 8%, and preferably, from 0 to 6%, and most preferably, from 0.001 to 2% by weight of the isotropic concentrate, including all ranges subsumed therein.

Polymeric viscosity aids are an optional ingredient suitable for use in the isotropic concentrate of the present invention. If used, preferred polymers are those generally classified as high molecular weight ethoxylated fatty acid esters. Illustrative examples include PEG 120 methyl glucose dioleate, PEG 18 glyceryloleate/cocoate, PEG 150 pentaerythritol tetrastearate, mixtures thereof or the like. The often preferred polymeric viscosity aid is PEG 150 pentaerythritol tetrastearate which is sold under the Versathix name by Croda. If used, such aids make up from 0.001 to 0.5%, and preferably, from 0.001 to 0.3%, and most preferably, from 0.01 to 0.2% by weight of the isotropic concentrate, including all ranges subsumed therein.

In another embodiment of the invention, less than 3.0% by weight sulfate is present in the end use composition of the present invention, preferably less than 1.0% by weight, and most preferably, no (0.0% by weight) sulfate. The isotropic concentrate, therefore, should be formulated such that upon dilution, the ingredients (e.g., sulfate) are at the levels desired in the end use composition.

As to anionic surfactants suitable for use in the isotropic concentrate and end use composition of the present invention (i.e., when more than acyl isethionate and acyl taurate is used), the anionic surfactant used can include aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$RO(CH_2CH_2O)_nSO_3M$ wherein R is an alkyl or alkenyl having 8 to 18 carbons, preferably 12 to 18 carbons, n has an average value of at least 1.0, preferably less than 5, and most preferably 1 to 4, and M is a solubilizing cation such as sodium, potassium, ammonium or substituted ammonium.

The anionic may also include alkyl sulfosuccinates (including mono- and dialkyl, e.g., $C_6$-$C_{22}$ sulfosuccinates); alkyl and acyl taurates (often methyl taurates), alkyl and acyl sarcosinates, sulfoacetates, $C_8$-$C_{22}$ alkyl phosphates and phosphonates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$R^1O_2CCH_2CH(SO_3M)CO_2M$;

and amide-MEA sulfosuccinates of the formula:

$R^1CONHCH_2CH_2O_2CCH_2CH(SO_3M)CO_2M$ wherein $R^1$ ranges from $C_8$-$C_{22}$ alkyl.

Sarcosinates are generally indicated by the formula:

$R^2CON(CH_3)CH_2CO_2M$, wherein $R^2$ ranges from $C_8$-$C_{20}$ alkyl.

Taurates used are generally identified by formula:

$R^3CONR^4CH_2CH_2SO_3M$ wherein $R^3$ is a $C_8$-$C_{20}$ alkyl, $R^4$ is a $C_1$-$C_4$ alkyl. M is a solubilizing cation as previously described.

The isethionates that may be used include $C_8$-$C_{18}$ acyl isethionates (including those which have a substituted head group). These esters are prepared by a reaction between alkali metal isethionate with mixed aliphatic fatty acids having from 6 to 18 carbon atoms and an iodine value of less than 20. Often at least 75% of the mixed fatty acids have from 12 to 18 carbon atoms and up to 25% have from 6 to 10 carbon atoms.

The acyl isethionate used may be an alkoxylated isethionate such as is described in Ilardi et al., U.S. Pat. No. 5,393,466, entitled "Fatty Acid Esters of Polyalkoxylated" isethonic acid; issued Feb. 28, 1995; hereby incorporated by reference. This compound has the general formula:

$R^5C$—$O(O)$—$C(X)H$—$C(Y)H$—$(OCH_2$—$CH_2)_m$—$SO_3M$ wherein $R^5$ is an alkyl group having 8 to 18 carbons, m is an integer from 1 to 4, X and Y are each independently hydrogen or an alkyl group having 1 to 4 carbons and M is a solubilizing cation as previously described.

In an embodiment of the invention, an anionic surfactant used is sodium lauroyl glycinate, sodium cocoyl glycinate, sodium lauroyl glutamate, sodium cocoyl glutamate, sodium lauroyl isethionate, sodium cocoyl isethionate, sodium methyl lauroyl taurate, sodium methyl cocoyl taurate or a mixture thereof. Such anionic surfactants are commercially available from suppliers like Galaxy Surfactants, Clariant, Sino Lion and Innospec. Sodium cocoyl isethionate, sodium methyl lauroyl taurate, sodium methyl lauroyl isethionate or mixtures thereof are the preferred anionics suitable for use.

Amphoteric surfactants suitable for use in the invention (which depending on pH can be zwitterionic) include sodium acyl amphoacetates, sodium acyl amphopropionates, disodium acyl amphodiacetates and disodium acyl amphodipropionates where the acyl (i.e., alkanoyl group) can comprise a $C_7$-$C_{18}$ alkyl portion. Illustrative examples of the amphoteric surfactants suitable for use include sodium lauroamphoacetate, sodium cocoamphoacetate, sodium lauroamphoacetate, sodium cocoamphoacetate and mixtures thereof.

As to the zwitterionic surfactants that may be employed in the present invention, such surfactants include at least one acid group. Such an acid group may be a carboxylic or a sulphonic acid group. They often include quaternary nitrogen, and therefore, can be quaternary amino acids. They should generally include an alkyl or alkenyl group of 7 to 18 carbon atoms generally comply with an overall structural formula:

$R^6$—[—$C(O)$—$NH(CH_2)_q$—]$_r$—$N^+$—$(R^7$—)($R^8$)A-B where $R^7$ is alkyl or alkenyl of 7 to 18 carbon atoms; $R^7$ and $R^8$ are each independently alkyl, hydroxyalkyl or carboxyalkyl of 1 to 3 carbon atoms; q is 2 to 4; r is 0 to 1; A is alkylene of 1 to 3 carbon atoms optionally substituted with hydroxyl, and B is —$CO_2$— or —$SO_3$—.

Suitable zwitterionic surfactants for use in the present invention and within the above general formula include simple betaines of formula:

$R^6$—$N^+$—$(R^7)(R^8)CH_2CO_2^-$ and amido betaines of formula:

$R^6$—$CONH(CH_2)_r$—$N^+$—$(R^7)(R^8)CH_2CO_2^-$ where t is 2 or 3.

In both formulae $R^6$, $R^7$ and $R^8$ are as defined previously. $R^6$ may, in particular, be a mixture of $C_{12}$ and $C_{14}$ alkyl groups derived from coconut oil so that at least half, preferably at least three quarters of the groups $R^6$ have 10 to 14 carbon atoms. $R^7$ and $R^8$ are preferably methyl.

A further possibility is that the zwitterionic surfactant is a sulphobetaine of formula:

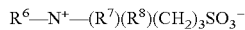

or

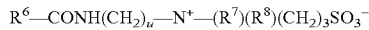

where u is 2 or 3, or variants of these in which —(CH$_2$)$_3$SO$_3^-$ is replaced by —CH$_2$C(OH)(H)CH$_2$SO$_3$.

In these formulae, R$^6$, R$^7$ and R$^8$ are as previously defined.

Illustrative examples of the zwitterionic surfactants suitable for use include betaines like cocodimethyl carboxymethyl betaine, cocamidopropyl betaine and laurylamidopropyl betaine. An additional zwitterionic surfactant suitable for use includes cocamidopropyl sultaine. Such surfactants are made commercially available from suppliers like Stepan Company, and it is within the scope of the invention to employ mixtures of the aforementioned surfactants. In a preferred embodiment, the zwitterionic surfactant used in this invention is cocamidopropyl betaine.

In an embodiment of the invention, cationic surfactants may optionally be used in the isotropic concentrate and end use composition of the present invention.

One class of optional cationic surfactants includes heterocyclic ammonium salts such as cetyl or stearyl pyridinium chloride, alkyl amidoethyl pyrrylinodium methyl sulfate, and lapyrium chloride.

Tetra alkyl ammonium salts are another useful class of cationic surfactants suitable for optional use. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides, and behenyl dimethyl ammonium chloride.

Still other types of cationic surfactants that may be used are the various ethoxylated quaternary amines and ester quats. Examples include PEG-5 stearyl ammonium lactate (e.g., Genamin KSL manufactured by Clariant), PEG-2 coco ammonium chloride, PEG-15 hydrogenated tallow ammonium chloride, PEG 15 stearyl ammonium chloride, dipalmitoyl ethyl methyl ammonium chloride, dipalmitoyl hydroxyethyl methyl sulfate, and strearyl amidopropyl dimethylamine lactate.

Even other useful cationic surfactants suitable for optional use include quaternized hydrolysates of silk, wheat, and keratin proteins, and it is within the scope of the invention to use mixtures of the aforementioned cationic surfactants.

If used, cationic surfactants will make up no more than 1.0% by weight of the end use composition. If present, they typically make up from 0.001 to 0.7%, and more typically, from 0.01 to 0.5% by weight of the end use composition, including all ranges subsumed therein.

In an embodiment of this invention, the compositions of this invention will be substantially free of polymeric quaternary ammonium compounds (including salts of the same). In another embodiment, the end use composition will comprise less than 0.1% by weight polymeric quaternary ammonium compounds. In yet another embodiment, the end use composition comprises less than 0.01% by weight polymeric quaternary ammonium compounds. In even another embodiment, the isotropic concentrate and end use composition are free of polymeric quaternary ammonium compounds (i.e., 0.0%).

Water preferably makes up from 25 to 80% by weight of the isotropic concentrate as previously noted, including all ranges subsumed therein.

The pH of the isotropic composition and end use composition is typically from 4.5 to 10, and preferably, from 5 to 9, and most preferably, from 5.2 to 7.5, including all ranges subsumed therein. Adjusters suitable to modify/buffer the pH may be used. Such pH adjusters include triethylamine, NaOH, KOH, H$_2$SO$_4$, HCl, C$_6$H$_8$O$_7$ (i.e., citric acid) or mixtures thereof. The pH adjusters are added at amounts to yield the desired final pH. The pH values may be assessed with commercial instrumentation such as a pH meter made commercially available from Thermo Scientific®.

Optional skin benefit agents suitable for use in this invention are limited only to the extent that they are capable of being topically applied, and suitable to dissolve in the hydratable composition and end use composition at the desired pH. Illustrative examples of the benefit agents suitable to include in the water portion of the compositions are acids, like amino acids, such as arginine, valine or histidine. Additional water soluble benefit agents suitable for use include vitamin B$_2$, niacinamide (vitamin B$_3$), vitamin B$_6$, vitamin C, mixtures thereof or the like. Water soluble derivatives of such vitamins may also be employed. For instance, vitamin C derivatives such as ascorbyl tetraisopalmitate, magnesium ascorbyl phosphate and ascorbyl glycoside may be used alone or in combination with each other. Other water soluble benefit agents suitable for use include 4-ethyl resorcinol, extracts like sage, aloe vera, green tea, grapeseed, thyme, chamomile, yarrow, cucumber, liquorice, rosemary extract or mixtures thereof. Water soluble sunscreens like ensulizole may also be used. Total amount of optional water soluble benefit agents (including mixtures) when present in the invention may range from 0.0 to 10%, preferably from 0.001 to 8%, and most preferably, from 0.01 to 6% by weight, based on total weight of the end use composition and including all ranges subsumed therein.

It is also within the scope of the present invention to optionally include oil (i.e., non-water) soluble benefit agents. The end use composition is substantially free of oil and preferably has less than 0.15% by weight oil, and most preferably, no oil (0.0%). Thus, oil soluble actives or benefit agents are solubilized in the surfactants used. The only limitation with respect to such oil soluble benefit agents are that the same are suitable to provide a benefit when topically applied.

Illustrative examples of the types of oil soluble benefit agents that may optionally be used in the compositions of this invention include components like stearic acid, vitamins like Vitamin A, D, E and K (and their oil soluble derivatives), sunscreens like ethylhexylmethoxycinnamate, bisethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Other optional oil soluble benefit agents suitable for use include resorcinols like 4-hexyl resorcinol, 4-phenylethyl resorcinol, 4-cyclopentyl resorcinol, 4-cyclohexyl resorcinol 4-isopropyl resorcinol or a mixture thereof. Also, 5-substituted resorcinols like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol mixtures thereof or the like. In an embodiment of the invention, the optional oil soluble benefit agent used is a retinoic acid precursor. In one embodiment of the invention, the retinoic acid precursor is retinol, retinal, retinyl propionate, retinyl palmitate, retinyl acetate or a mixture thereof. Retinyl propionate, retinyl palmitate and mixtures thereof are typically preferred. Still another retinoic acid precursor suitable for use is hydroxyanasatil retinoate made commercially available under the name Retextra® as supplied by Molecular Design International. The same may be used in a mixture with the oil soluble actives described herein.

When optional (i.e., 0.0 to 1.5% by weight) oil soluble active is used in the end use composition of the invention, it typically makes up from 0.001 to 1.5%, and in another embodiment, from 0.05 to 1.2%, and in yet another embodiment, from 0.1 to 0.5% by weight of the total weight of the end use composition, including all ranges subsumed therein.

Preservatives can desirably be incorporated into the hydratable concentrate and end use composition to protect against the growth of potentially harmful microorganisms. Cosmetic chemists are familiar with appropriate preservatives and routinely choose them to satisfy the preservative challenge test and to provide product stability. Suitable traditional preservatives for use include hydantoin derivatives and propionate salts. Particularly preferred preservatives are iodopropynyl butyl carbamate, phenoxyethanol, 1,2-octanediol, hydroxyacetophenone, ethylhexylglycerine, hexylene glycol, methyl paraben, propyl paraben, imidazolidinyl urea, sodium dehydroacetate, dimethyl-dimethyl (DMDM) hydantoin and benzyl alcohol and mixtures thereof. Other preservatives suitable for use include sodium dehydroacetate, chlorophenesin and decylene glycol. The preservatives should be selected having regard for the use of the composition and possible incompatibilities between the preservatives and other ingredients in the emulsion. Preservatives are preferably employed in amounts ranging from 0.01% to 2.0% by weight of the total weight of the end use composition (up to 7% by weight of total isotropic concentrate), including all ranges subsumed therein. Also preferred is a preservative system with hydroxyacetophenone alone or in a mixture with other preservatives.

Thickening agents are optionally suitable for use in the compositions of the present invention. Particularly useful are the polysaccharides. Examples include fibers, starches, natural/synthetic gums and cellulosics. Representative of the starches are chemically modified starches such as sodium hydroxypropyl starch phosphate and aluminum starch octenylsuccinate. Tapioca starch is often preferred, as is maltodextrin. Suitable gums include xanthan, sclerotium, pectin, karaya, arabic, agar, guar (including Acacia senegal guar), carrageenan, alginate and combinations thereof. Suitable cellulosics include hydroxypropyl cellulose, hydroxypropyl methylcellulose, ethylcellulose, sodium carboxy methylcellulose (cellulose gum/carboxymethyl cellulose) and cellulose (e.g. cellulose microfibrils, cellulose nanocrystals or microcrystalline cellulose). Sources of cellulose microfibrils include secondary cell wall materials (e.g. wood pulp, cotton), bacterial cellulose, and primary cell wall materials. Preferably the source of primary cell wall material is selected from parenchymal tissue from fruits, roots, bulbs, tubers, seeds, leaves and combination thereof; more preferably is selected from citrus fruit, tomato fruit, peach fruit, pumpkin fruit, kiwi fruit, apple fruit, mango fruit, sugar beet, beet root, turnip, parsnip, maize, oat, wheat, peas and combinations thereof; and even more preferably is selected from citrus fruit, tomato fruit and combinations thereof. A most preferred source of primary cell wall material is parenchymal tissue from citrus fruit. Citrus fibers, such as those made available by Herbacel® as AQ Plus can also be used as source for cellulose microfibrils. The cellulose sources can be surface modified by any of the known methods including those described in Colloidal Polymer Science, Kalia et al., "Nanofibrillated cellulose: surface modification and potential applications" (2014), Vol 292, Pages 5-31. Synthetic polymers, in addition to polymeric viscosity aids, are yet another class of effective thickening agents that can optionally be used. This category includes crosslinked polyacrylates such as the Carbomers, polyacrylamides such as Sepigel® 305 and taurate copolymers such as Simulgel® EG and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100. Calcium carbonate, fumed silica, and magnesium-aluminum-silicate may also be used.

The amounts of optional thickening agent, when used, may range from 0.001 to 6%, by weight of the compositions. Maltodextrin, xanthan gum, and carboxymethyl cellulose are the often preferred optional thickening agents.

Fixatives, chelators (like EDTA) and exfoliants may optionally be included in the compositions of the present invention. Each of these substances may range from about 0.03 to about 5%, preferably between 0.1 and 3% by weight of the total weight of the end use composition, including all ranges subsumed therein. To the extent the exfoliants are used, those selected should be of small enough particle size so that they do not impede the performance of any packaging used to dispense the compositions of this invention.

As to the emulsifiers used in the invention, these have an HLB from 8 to 19. Illustrative examples include Tween, 40, 60, 80, polysorbate 20 (HLB 16.7), PEG-100 stearate, cocamide MEA, PEG-8 oleate, laureth-23 or mixtures thereof. Emulsifiers in the isotropic concentrate of the present invention will make up from 0.7 to 5% by weight of the isotropic concentrate, including all ranges subsumed therein. As used herein, polysorbate 20 is herein defined as an emulsifier and often the preferred emulsifier in the compositions of the present invention.

Conventional humectants in addition to glycerin may be employed as additives in the present invention to assist in moisturizing skin when end use composition is topically applied. These are generally polyhydric alcohol type materials. Typical polyhydric alcohols in addition to glycerin include propylene glycol, dipropylene glycol, polypropylene glycol (e.g., PPG-9), polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is humectant that is at least 75% by weight glycerin based on total weight of humectant in the compositions.

Mixtures of propylene glycol and glycerin are often preferred where such mixture is from 5 to 15%, and preferably 6 to 12% by weight propylene glycol based on total weight of polypropylene glycol and glycerol in the humectant. The amount of humectant employed in addition to glycerin may range anywhere from 0.0 to 35% by weight of the total weight of the end use composition. Often, additional humectant makes up from 0.0 to 20%, and preferably, from 0.001 to 15% by weight (most preferably, from 2 to 12% by weight) of the total weight of the end use compositions.

As to the isotropic concentrate of the present invention, the same typically has from 5 to 50% by weight humectant, including all ranges subsumed therein. In an embodiment of the invention, at least 85% by weight, and preferably, 90 to 100 percent by weight total humectant used in the isotropic concentrate and end use composition is glycerin.

The fragrances used in the present invention include art recognized fragrances suitable for use in compositions that are topically applied. Such fragrances can include components like nerolidol, geraniol, terpinolene, linalool, terpinene, limonene, pinene, camphene, citronellol, citronellal, geraniol, vanillin, terpineol, thymol, eugenol, lavender oil, sage oil, orange flower oil, rosemary oil, ginger oil, lemon oil, thyme oil, terpinyl acetate, mixtures thereof or the like. Unexpectedly, it has been discovered that when conventional fragrance is used with emulsifier as described in the present invention, the isotropic concentrate and end use composition of the present invention are free of ingredient precipitation. Typically, the isotropic concentrate will comprise from 0.7 to 8% by weight fragrance, including all ranges subsumed therein.

The present invention is directed to isotropic concentrated compositions that reduce in viscosity when mixed with water.

When making isotropic concentrate composition of the present invention, the desired ingredients may be mixed with conventional apparatus under moderate shear and atmospheric conditions, with temperature being from 35 to 80° C. Water is added to the isotropic concentrated composition to produce the end use composition. Moderate shear such as shaking (or stirring) in a container will yield the end use composition in less than 5 minutes, preferably in less than 3 minutes, and most preferably, in less than 2 minutes. In an embodiment of the invention, end use composition is made in less than 1 minute, even preferably, less than 30 seconds.

The packaging for the compositions typically is not limited as long as isotropic concentrate composition can be hydrated and end use composition can be made upon the addition of water. In an embodiment on the invention, isotropic concentrate is sold in a pouch or cartridge that is associated with and inserted in a bottle or canister. The bottle or canister is one which is filled with water and allows for the release of the concentrate into the same for mixing with the water. Typically, the bottle or canister has a cap with a pump that opens the sachet or canister to release the concentrate into the water to make end use composition. Such a concentrate unexpectedly yields an end use composition, such as a hand wash, with desirable characteristics appreciated by consumers and with no precipitate or graininess. Such packaging allows for infinite numbers of refilling to invariably reduce plastic waste in the environment. The packaging may also be equipped with a mesh fit in its exit orifice to release end use composition in the form of a foam. Conventional pumps having mesh with holes from 35 to 140 microns prior to exiting the pump are made commercially available from suppliers like Albea and Rieke.

The Examples provided are to facilitate an understanding of the invention. They are not intended to limit the scope of the claims.

EXAMPLE I

The composition represented in this Example as set forth in the Table was made by conventional means, and therefore, by mixing ingredients with moderate shear under atmospheric conditions at a temperature from about 35 to 75° C. The pH of the resulting isotropic concentrate was about 6.9 and the viscosity was about 100 cps.

TABLE

| Isotropic Concentrate Composition | % weight in isotropic concentrate |
|---|---|
| Ingredient | |
| Water | Balance |
| Glycerin | 25 |
| Sodium Cocoyl Isethionate | 3.3 |
| Methyl lauroyl taurate | 3.3 |
| Lauric Acid | 0.3 |
| Stearic Acid | 0.5 |
| Preservative | 5.0 |
| PPG-9 | 2.5 |
| Cocamidopropyl Betaine (UQS) | 13.3 |
| Polysorbate 20 | 2.3 |
| Fragrance | 3.5 |
| NaOH | 0.8 |
| Citric Acid | 0.02 |
| Total | 100 |

The isotropic concentrate composition was hydrated/diluted with 3 parts water for every 1 part concentrate. The resulting end use composition, made with agitation in under 1 minute, was a foamable hand wash composition suitable for use in a refillable package. The hand wash composition had a viscosity of about 50 cps. Surprisingly, neither the concentrate nor the hand wash composition displayed any visible or physical signs of precipitate or crystallization after 48 to 72 hours at room temperature (25° C.). Further, a conventional foam pump dispenser was charged with the hand wash composition of the present invention. With no signs of clogging from precipitate, the pump dispenser discharged about 1 milliliter of hand wash composition per pump through a mesh of about 100 microns to thereby produce a foam hand washing composition.

EXAMPLE II

In this Example, an isotropic concentrate composition was made that was similar to the concentrate prepared in Example I except that no fragrance and no emulsifier were included, water to balance. End use composition was also made by diluting the concentrate in the manner described in Example I. The resulting concentrate and end use composition prepared in this Example displayed precipitate/crystallization in less than 24 hours at room temperature (25° C.). Both were unacceptable for consumer use.

What is claimed is:
1. An end use composition made by hydrating with water an isotropic concentrate composition having a viscosity from 30 to 6,500 cps, a pH from 5.2 to 7.5 and comprising:
  i) 0.1 to 10% by weight of an acyl isethionate:
  ii) 0.1% to 10% by weight of an acyl taurate;
  iii) 0.2 to 25% by weight of an amphoteric and/or zwitterionic surfactant;
  iv) 5.0 to 50% by weight of humectant comprising glycerin:
  v) 0.7 to 8% by weight fragrance;
  vi) 0.7 to 5% by weight emulsifier having an HLB from 8 to 19; and
  vii) 25 to 80% by weight water wherein total surfactant makes up from 12 to 35% by weight of the isotropic concentrate composition and further wherein emulsifier to fragrance are at a weight ratio from 1:0.8 to 1:4 and the isotropic concentrate composition when hydrated forms the end use composition comprising no sulfate based surfactant and the isotropic concentrate composition is hydrated with water at an isotropic concentrate composition to water ratio from 1:1 to 1:6, the isotropic concentrate composition does not increase in viscosity after hydration ; wherein the acyl isethionate and acyl taurate make up from 75 to 100% of total anionic surfactant and wherein the end use composition is dispensable as a foam from a pump dispenser.

2. The end use composition according to claim 1 wherein the end use composition is a hand wash composition for use in a refillable package and the acyl isethionate is sodium cocoyl isethionate and the acyl taurate is sodium methyl lauroyl taurate, the isotropic concentrate composition having a viscosity from 50 to 3,000 cps.

3. The end use composition according to claim 1 wherein the end use composition is free of precipitate and comprises thymol and terpineol.

4. The end use composition according to claim 1 wherein the emulsifier comprises polysorbate 20.

5. The end use composition according to claim 1 wherein the isotropic concentrate composition comprises from 0.5 to 6% by weight acyl isethionate, from 0.5 to 6% by weight acyl taurate, 3 to 20% by weight zwitterionic surfactant, 1 to 7% by weight fragrance and 10 to 40% by weight humectant comprising glycerin.

6. The end use composition according to claim 1 wherein the emulsifier and to fragrance are at an emulsifier to fragrance weight ratio from 1:1 to 1:3.

7. The end use composition according to claim 1 wherein the isotropic concentrate composition further comprises from 0.1 to 3% by weight myristic acid, auric acid, stearic acid, an alcohol derivative thereof or mixture thereof.

8. The end use composition according to claim 1 wherein the end use composition further comprises a sunscreen, vitamin $B_2$, niacinamide, vitamin $B_6$, vitamin C, a resorcinol, aloe vera, extracts of sage, green tea, grapeseed, thyme, chamomile, yarrow, cucumber, liquorice, rosemary extract or mixtures thereof.

9. The end use composition according to claim 1 wherein the end use composition further comprises 12-hydroxystearic acid, stearic acid, vitamin A, D, E and/or K, omega-3 fatty acid, omega-6 fatty add, dimbazole, farnesol, ursolic acid, geranyl geraniol, oleyl betaine, cocoyl hydroxyethyl imidazoline, hexanoyl sphingosine, petroselinic acid, conjugated linaleic acid or a mixture thereof.

10. The end use composition according to claim 1 wherein the end use composition further comprises 1,2-octanediol, hydroxyacetophenone, ethylhexylglycerine, hexylene glycol, benzyl alcohol or a mixture thereof.

11. The end use composition according to claim 1 wherein the isotropic concentrate composition comprises a thickener or a pH adjuster.

12. The end use composition according to claim 11 wherein the end use composition has a viscosity that is lower than viscosity of the isotropic concentrate composition after the isotropic concentrate composition is hydrated.

13. The end use composition according to claim 12 wherein the end use composition comprises less than 1.0% by weight sulfate based surfactant, less than 0.3% by weight oil other than fragrance oil, and has a pH from 5.2 to about 6.9.

* * * * *